(12) United States Patent
Kondis (10) Patent No.: US 10,864,075 B2
(45) Date of Patent: Dec. 15, 2020

(54) INTRAOCULAR LENS VISUALIZATION AND TRACKING SYSTEM

(71) Applicant: RxSight, Inc., Aliso Viejo, CA (US)

(72) Inventor: John Kondis, Irvine, CA (US)

(73) Assignee: RxSight, Inc., Aliso Viejo, CA (US)

( * ) Notice: Subject to any disclaimer, the term of this patent is extended or adjusted under 35 U.S.C. 154(b) by 221 days.

(21) Appl. No.: 15/859,653

(22) Filed: Dec. 31, 2017

(65) Prior Publication Data

US 2019/0201188 A1 Jul. 4, 2019

(51) Int. Cl.
*A61F 2/16* (2006.01)
*G02B 21/20* (2006.01)
*G02B 21/06* (2006.01)
*G02B 21/36* (2006.01)

(52) U.S. Cl.
CPC ............ *A61F 2/16* (2013.01); *G02B 21/06* (2013.01); *G02B 21/20* (2013.01); *A61F 2250/0001* (2013.01); *G02B 21/365* (2013.01)

(58) Field of Classification Search
CPC ......... A61B 3/14; A61B 3/107; A61B 3/0025; A61B 3/10; A61B 3/102; A61B 3/1173; A61B 3/152; A61B 3/1015; A61B 3/117; A61B 3/156; A61B 3/0008; A61B 3/132
See application file for complete search history.

(56) References Cited

U.S. PATENT DOCUMENTS

| | | | |
|---|---|---|---|
| 4,955,904 A * | 9/1990 | Atebara | A61F 2/1613 623/6.17 |
| 5,532,770 A * | 7/1996 | Schneider | A61F 2/16 351/205 |
| 6,450,642 B1 | 9/2002 | Jethmalani et al. | |
| 6,486,943 B1 | 11/2002 | Burns et al. | |
| 8,711,364 B2 * | 4/2014 | Brennan | A61B 3/102 356/479 |
| 9,950,482 B2 | 4/2018 | Grubbs et al. | |
| 2005/0018136 A1 * | 1/2005 | Hayashi | A61B 3/103 351/212 |
| 2005/0041207 A1 * | 2/2005 | Miller | A61B 3/156 351/200 |
| 2010/0082017 A1 * | 4/2010 | Zickler | A61F 2/16 606/4 |

(Continued)

FOREIGN PATENT DOCUMENTS

WO WO 01/85016 A2 11/2001

*Primary Examiner* — Christopher Stanford (57) ABSTRACT

An ophthalmic visualization system includes a rear illumination system, to generate and to project a rear illumination light onto a retina of an eye that has an intraocular lens (IOL) implanted into the eye, so that the rear illumination light reflects from the retina as a reflected illumination light, wherein a central portion of the reflected illumination light propagates through the IOL to form an IOL-focused illumination light, and a peripheral portion of the reflected illumination light propagates around the IOL to form a peripheral illumination light; an optic, to receive the IOL-focused illumination light and the peripheral illumination light from the eye, and to transmit the received illumination lights; an aperture slop, to stop the transmitted peripheral illumination light, and to allow the IOL-focused illumination light to pass through; and an imaging system, to form an isolated IOL image based on the transmitted IOL-focused illumination light.

16 Claims, 11 Drawing Sheets

(56) References Cited

U.S. PATENT DOCUMENTS

| | | | |
|---|---|---|---|
| 2010/0134760 A1* | 6/2010 | Salvati | A61B 3/0025 351/206 |
| 2010/0231858 A1* | 9/2010 | Su | G01J 9/00 351/212 |
| 2010/0274228 A1* | 10/2010 | Mrochen | A61F 9/013 604/541 |
| 2011/0190740 A1* | 8/2011 | Frey | A61F 9/00825 606/5 |
| 2011/0292340 A1* | 12/2011 | Shimizu | A61B 3/10 351/206 |
| 2012/0197102 A1* | 8/2012 | Hanebuchi | A61F 2/16 600/398 |
| 2013/0050643 A1* | 2/2013 | Endo | A61B 3/1035 351/206 |
| 2013/0102895 A1* | 4/2013 | Gooding | A61B 3/10 600/426 |
| 2014/0028977 A1* | 1/2014 | Umekawa | A61B 3/152 351/208 |
| 2014/0028978 A1* | 1/2014 | Sakagawa | A61B 3/152 351/208 |
| 2014/0074074 A1* | 3/2014 | Dick | A61F 9/00825 606/6 |
| 2014/0268045 A1* | 9/2014 | Bor | A61B 3/14 351/206 |
| 2014/0313480 A1* | 10/2014 | Ohta | A61B 3/10 351/206 |
| 2014/0313485 A1* | 10/2014 | Umekawa | A61B 3/0008 351/211 |
| 2014/0340635 A1* | 11/2014 | Oyaizu | A61B 3/107 351/206 |
| 2014/0375951 A1 | 12/2014 | Barth et al. | |
| 2015/0131054 A1* | 5/2015 | Wuellner | A61B 3/0025 351/211 |
| 2016/0089271 A1* | 3/2016 | Zacharias | A61F 9/00834 606/5 |
| 2017/0027437 A1* | 2/2017 | Neal | A61B 3/0025 |
| 2019/0159889 A1* | 5/2019 | Kondis | A61F 2/16 |
| 2019/0167474 A1* | 6/2019 | Artsyukhovich | A61F 2/1662 |

* cited by examiner

INTRAOCULAR LENS VISUALIZATION AND TRACKING SYSTEM

TECHNICAL FIELD

This invention relates to an ophthalmic visualization system, and more specifically to an intraocular lens visualization and tracking system.

BACKGROUND

Ophthalmic surgical systems have been experiencing revolutionary growth in the last couple decades. Ultrasound-based phacoemulsification drove a first wave of transformative changes in cataract surgery. This was followed by a femtosecond laser-based second wave of new cataract surgical devices. The newer and newer generations of devices supersede the previous generations by improving the precision and control they provide for the operating surgeon or doctor.

One limitation that remained in spite of all these developments, is the problem of the last diopter. Even if intraocular lenses (IOLs) are inserted into the eye with the highest precision and control, the healing process that takes place after the surgery sometimes moves, tilts or rotates the intraocular lenses by several tenths of a millimeter in a notable fraction of the cases, thus changing the effective optical power of the eye by a diopter or more.

This substantial challenge has been targeted by the introduction of light adjustable intraocular lens technology, as described in U.S. Pat. No. 6,450,642, "Lenses capable of post-fabrication power modification", by Jethmalani et al., and in U.S. patent application Ser. No. 15/159,909, "Method for modifying power of light adjustable lens", by Grubbs et al., among others, both hereby incorporated in their entirety by reference. This innovation introduced Light Adjustable IOLs, formed from a photosensitive polymer, that change their shape when irradiated with an appropriate ultraviolet light. A suitable change in the shape of the IOL changes its optical power. This radically new aspect of the Light Adjustable IOLs enables the doctor to change the optical power of the inserted IOLs non-invasively long after the surgery has been completed. These light adjustable lenses thus make doctors capable of compensating the unplanned changes of the optical power of the inserted IOLs after they settled in the capsular bag of the eye, and thus to finalize the IOL with the optimal last diopter.

In some detail, after the IOL is implanted in the capsular bag, the healing moves, rotates, or tilts, together referred to as shifts, the IOL away from the planned location. This shift can lead to the IOL optically underperforming relative to the planned, expected, or promised outcome. The implanted IOL can also optically underperform if the pre-surgical planning did not identify the IOL most appropriate for the patient. The light adjustable lens technology can mitigate this underperformance. The process starts with the doctor calling the patient back some time after the surgery for an office visit. At this visit, the doctor measures the underperformance of the IOL that developed for any of the above reasons. Next, the doctor determines how to change the IOL optical characteristics (its shape and index of refraction) to compensate the measured optical underperformance. With this determination, the doctor adjusts the IOL by irradiating the implanted and shifted IOL with an ultraviolet light with an intensity profile designed to induce the determined change of optical characteristics. Finally, the changed characteristics of the irradiated IOL is locked in by a subsequent procedure to prevent any further changes. The described light adjustment procedure of these light-adjustable IOLs promises to substantially increase much-improved visual outcomes and patient satisfaction with cataract surgeries.

For this light adjustable technology to work, the location of the IOL needs to be determined precisely inside the capsular bag, so that the adjusting light and its intensity profile can be aligned with the IOL with high precision. Presently, this determination and alignment is done visually by the doctor using a binocular microscope. However, the actual image of the IOL can have limited contrast and a limited signal-to-noise ratio. If electronic displays are used, the image can be grainy, with hard-to-identify contours. Noise, limited contrast, and unclear contours can make the recognition of the edge of the IOL, and thus the determination of its location challenging for the surgeon in a fraction of the cases.

For at least these reasons, new systems and methods are desirable to locate the implanted IOL with higher precision, thus enabling the adjustment of the light adjustable lenses with high precision, and thus materializing their full potential.

SUMMARY

The above-described needs are addressed by embodiments of an ophthalmic visualization system that comprises a rear illumination system, to generate and to project a rear illumination light onto a retina of an eye that has an intraocular lens (IOL) implanted into the eye, so that the rear illumination light reflects from the retina as a reflected illumination light, wherein a central portion of the reflected illumination light propagates through the IOL to form an IOL-focused illumination light, and a peripheral portion of the reflected illumination light propagates around the IOL to form a peripheral illumination light; an optic, to receive the IOL-focused illumination light and the peripheral illumination light from the eye, and to transmit the received illumination lights; an aperture stop, to stop the transmitted peripheral illumination light, and to allow the IOL-focused illumination light to pass through; and an imaging system, to form an isolated IOL image based on the transmitted IOL-focused illumination light.

In some embodiments, the imaging system comprises a camera, and possibly an associated image recognition system with a processor, to determine a location of the IOL from the isolated IOL image in an optic reference frame.

In some embodiments, a method of tracking an intraocular lens, comprises rear-illuminating an eye that has an implanted intraocular lens (IOL), with an ophthalmic visualization system by generating a rear illumination light with a rear illumination system and projecting the rear illumination light with an optic onto a retina of the eye, so that a portion of the rear illumination light reflects from the retina as a reflected illumination light- wherein a central portion of the reflected illumination light propagates through the IOL to form an IOL-focused illumination light, and a peripheral portion of the reflected illumination light propagates around the IOL to form a peripheral illumination light; receiving and transmitting the IOL-focused illumination light and the peripheral illumination light by the optic; stopping the transmitted peripheral illumination light by an aperture stop; allowing the transmitted IOL-focused illumination light to pass through by the aperture stop, and forming an isolated IOL image based on the transmitted IOL-focused illumination light by an imaging system.

DETAILED DESCRIPTION

To address the issues above, embodiments of the invention include an ophthalmic visualization system that visualizes and tracks an IOL in a dilated pseudophakic patient. The ophthalmic visualization system provides an IOL image with a remarkably high contrast, and a high signal-to-noise ratio, and thus can be used to capture the location of the IOL relative to an ophthalmic reference without the need to implement a sophisticated edge-recognition algorithm, or without the doctor straining to visually determine the location of the IOL from a grainy, low signal-to-noise ratio image. Therefore, embodiments of these ophthalmic visualization systems, when used in conjunction with the devices that irradiate light adjustable implanted IOLs, enable doctors to deliver visual outcomes of cataract surgeries with a higher precision in a higher percentage of the cataract surgeries.

Figure 1A:
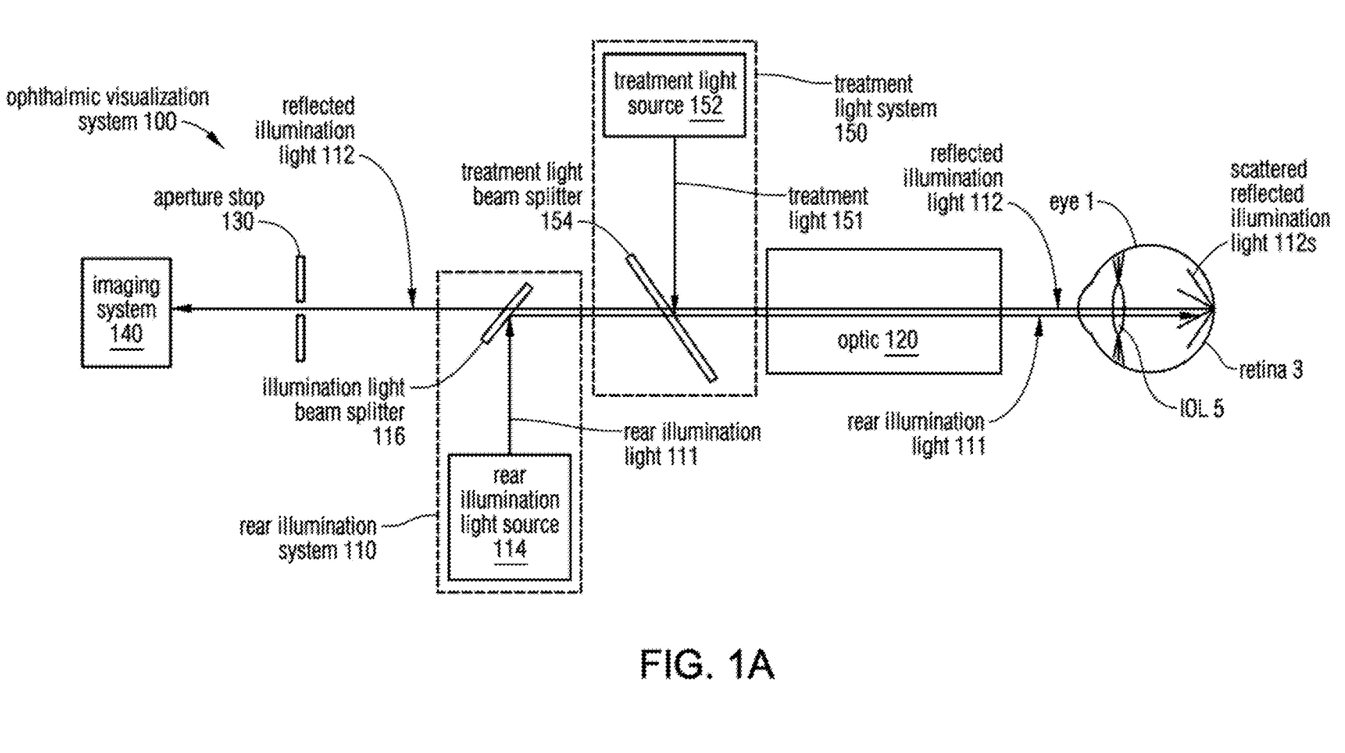
FIGS. 1A-B illustrate embodiments of an ophthalmic visualization system.

FIG. 1A illustrates an exemplary ophthalmic visualization system 100 that includes a rear illumination system 110, to generate a rear illumination light 111, and to project the rear illumination light 111 with an optic 120 towards an eye 1. The optic 120 can project the rear illumination light 111 onto a retina 3 of the eye 1 that has an intraocular lens (IOL) 5 implanted into the eye 1, so that the rear illumination light 111 illuminates a spot on the retina 3 and reflects from the retina 3 as a reflected illumination light 112. In general, the rear illumination light 111 scatters in a wide spatial angle as a scattered reflected illumination light 112s, and only a portion of it leaves the eye 1 as the reflected illumination light 112.

Figure 2A:
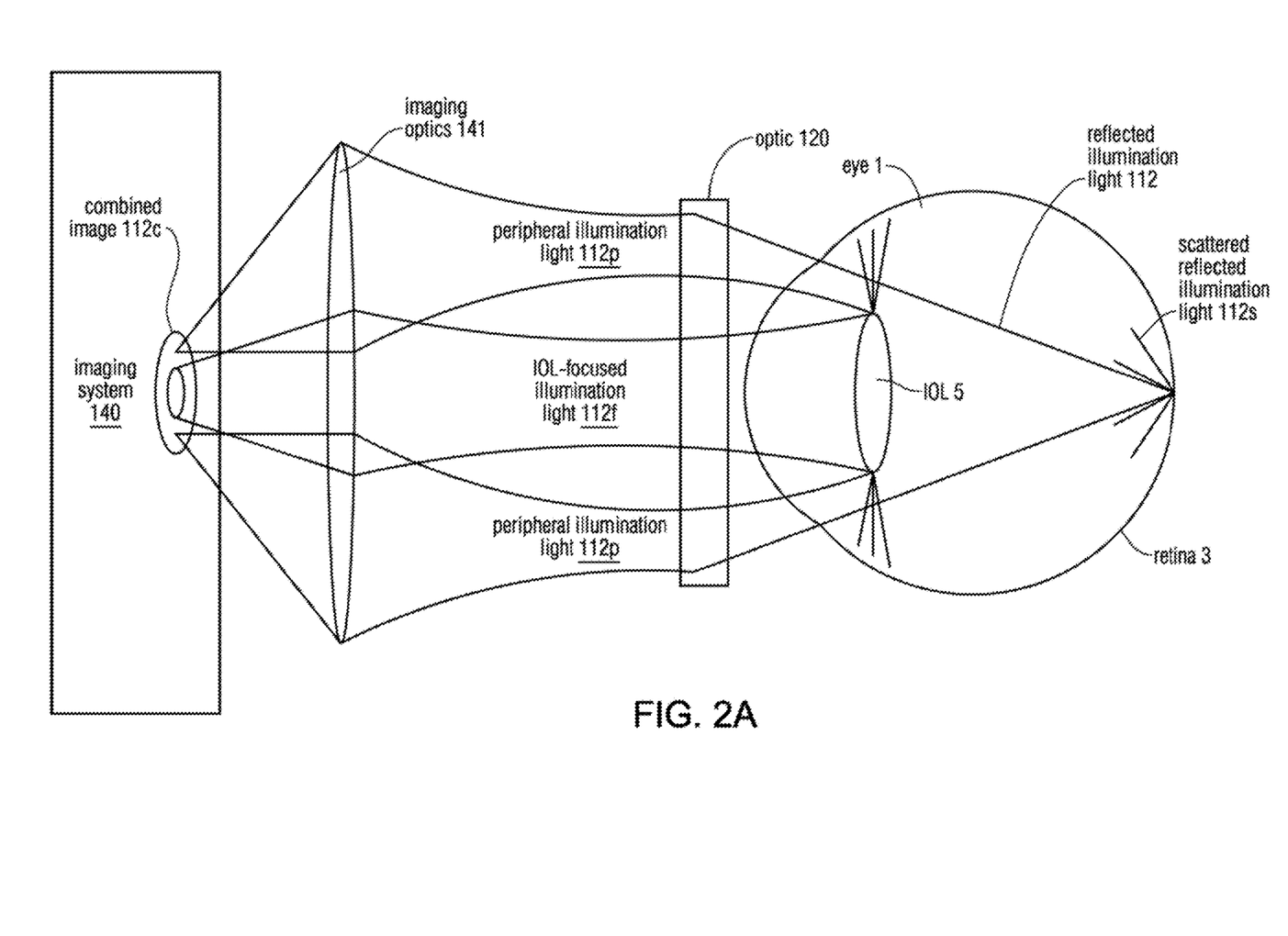
FIGS. 2A-B illustrate portions of the reflected illumination light and the image they generate.

FIG. 2A illustrates, that the reflected illumination light 112 is the portion of the scattered reflected illumination light 112s that is reflected from the retina 3 back towards the IOL 5 at such spatial angles that allow this reflected illumination light 112 to eventually leave the eye 1 through the pupil of the eye 1, thus providing an illumination light for the IOL 5 from behind. Some treatises call this the red reflex, or infrared (IR) reflex.

As FIG. 2A shows, in embodiments a central portion of the reflected illumination light 112 propagates through the IOL 5 to form an IOL-focused illumination light 112f, and a peripheral portion of the reflected illumination light 112 propagates around the IOL 5 to form a peripheral illumination light 112p. Both the IOL-focused illumination light 112f and the peripheral illumination light 112p can be received by the optic 120, that can transmit the received illumination lights 112f and 112p, as shown in both FIG. 1A and FIG. 2A, toward an imaging system 140. The imaging system 140 can include an imaging optics 141 that images these incoming illumination lights 112f and 112p onto an imaging plane, where they can form a combined image 112c that displays both the IOL 5 and its periphery, indicated by concentric circles.

Figure 2B:
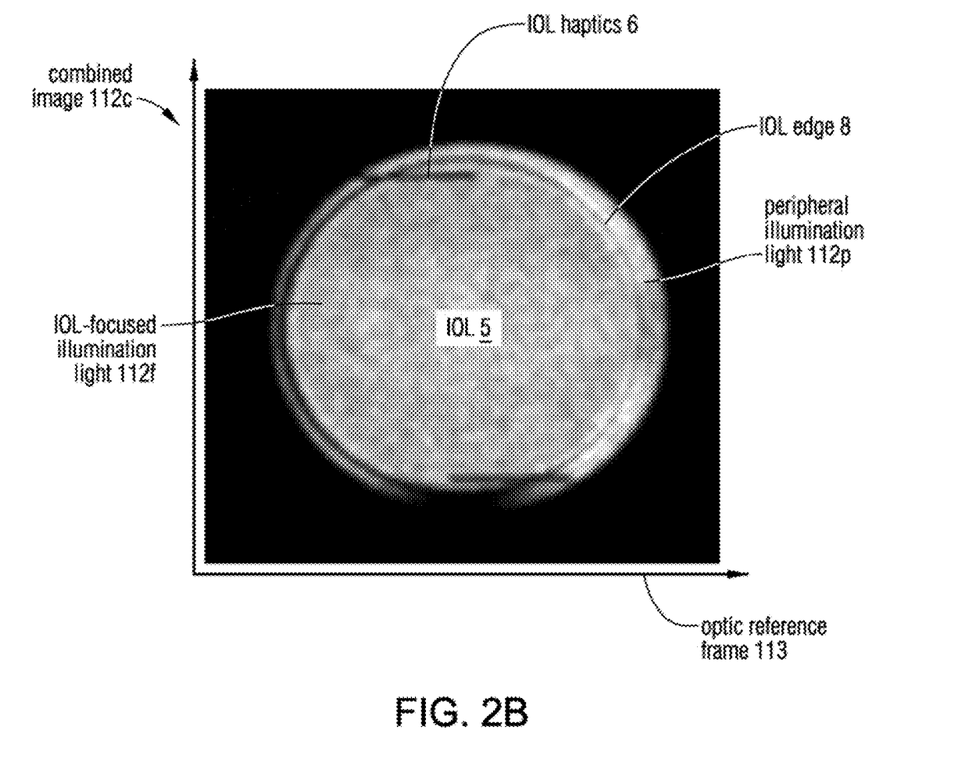

FIG. 2B illustrates an example of such a combined image 112c. The combined image 112c can include an image of the IOL 5, formed by the IOL-focused illumination light 112f, and an image of the periphery around the IOL 5, formed by the peripheral illumination light 112p. The image of IOL haptics 6 is also visible.

As described earlier, in some embodiments a treatment light system 150 can be combined with the ophthalmic visualization system 100 to generate a treatment light 151 by a treatment light source 152, and to redirect the treatment light 151 by a treatment light beam splitter 154 through the optic 120 to the eye 1. In such embodiments, a precise knowledge of the location of the IOL 5 in an optic reference frame 113 is needed for directing the light to its intended location with the optic 120 with high precision. The optic reference frame 113 can be defined relative to the optic 120, or relative to the imaging system 140.

As mentioned earlier, in automated implementations of the ophthalmic visualization system 100, combined with the treatment light system 150, often the doctor determines the location of the IOL 5 in a microscope visually, by identifying the location of its perimeter in the combined image 112c. However, the microscope image quality may be poor, making this identification challenging.

In some video-microscope-based digital embodiments, an edge recognition software can be implemented and used to find an IOL edge 8 in the combined image 112c, and to identity the IOL location from that. However, the edge recognition software may experience multiple challenges and has a substantial chance of not recognizing the edge location correctly because of potential obstacles as follows. First, in the combined image 112c the shade contrast of the edge can vary substantially; in the shown case from the right to the left. Second, the shade contrast can be very weak, in the shown image on the right, endangering a successful edge recognition. Third, in some cases, the signal-to-noise ratio can be quite poor. Fourth, the edge recognition software can get disoriented if an edge it is tracking seems to split into two, or is intersected, which is the ease where the IOL haptics 6 split from the IOL edge 8. For at least the here-listed reasons, the edge recognition software may not recognize the IOL edge 8 correctly, and thus may not deliver the IOL location with high enough reliability to base the projecting of the treatment light 151 on its result.

In non-automated video-microscope-based implementations, the doctor determines the location of the IOL 5 by visually examining the combined image 112c. For reasons analogous to the above, the doctor may also find it challenging to identify the IOL edge 8 in noisy, poor-contrast, strongly varying combined images 112c, or worse, may misidentify the IOL edge 8. At least for these reasons, new solutions are needed to improve the precision of IOL edge recognition.

Embodiments of the ophthalmic visualization system 100 deliver such a needed new solution based on the recognition that the IOL-focused illumination light 112f is refracted substantially by the optical power of the IOL 5, which can be around 20 Diopters, whereas the peripheral illumination light 112p does not suffer a comparable refraction. This substantial difference in the refractive power experienced along their optical paths separates these two lights 112*f* and 112*p* spatially along an interval of the optical pathway, as shown in FIG. 2A.

Figure 3A:
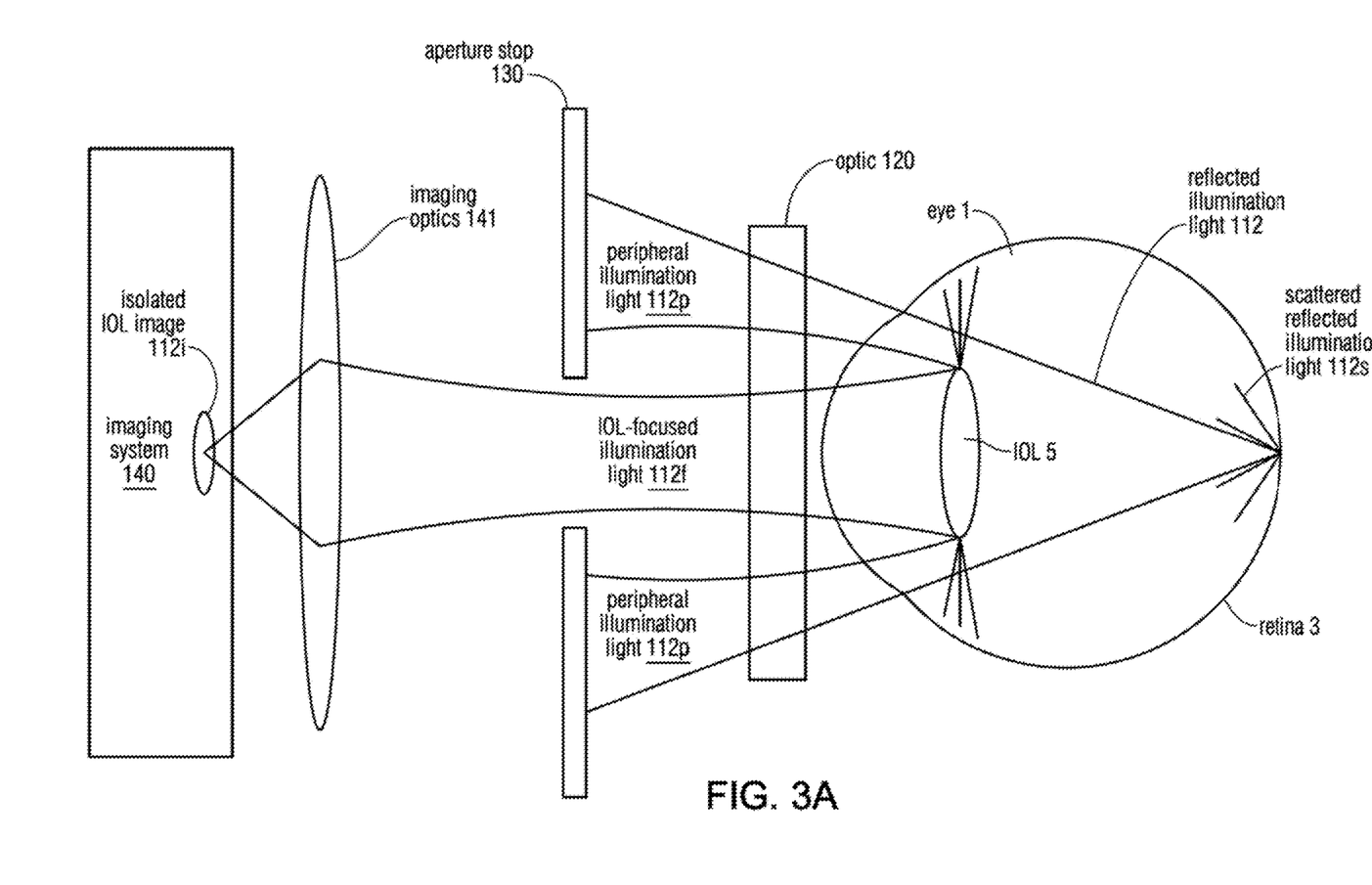
FIGS. 3A-C illustrate portions of the reflected illumination light and the image they generate in the presence of an aperture stop.

FIG. 1A and FIG. 3A illustrate that some embodiments of the ophthalmic visualization system 100 can exploit this fact to deliver the needed solution by including an aperture stop 130 somewhere along this interval of beam separation, to stop the transmitted peripheral illumination light 112*p*, while at the same time to allow the IOL-focused illumination light 112*f* to pass through. The aperture stop 130 can be an annulus, or a disc with a hole in its center. The inner diameter of the aperture stop 130, or the diameter of the hole in the center of its disc, can be large enough to let the entire IOL-focused illumination light 112*f* through, while the outer diameter of the disc of the aperture stop 130 can be large enough to block most, or all, the peripheral illumination light 112*p*. In such ophthalmic visualization systems 100, only the IOL-focused illumination light 112*f* reaches the imaging system 140, through the imaging optics 141, which in response can form an isolated IOL image 112*i*, based on the transmitted IOL-focused illumination light 112*f* alone. In some sense, the aperture stop 130 can be similar in operation to a Lyot stop.

Figure 3B:
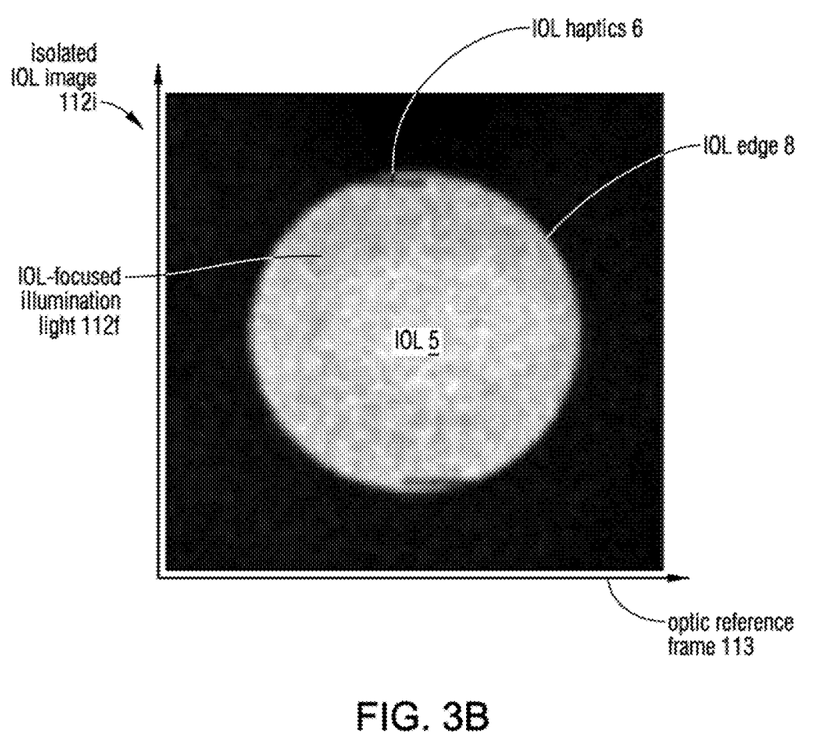

FIG. 3B shows such an isolated IOL image 112*i*. Notably, the IOL-focused illumination light 112*f* forms the isolated IOL image 112*i*, showing only the IOL 5, while the rest of the image field is dark. Clearly, the isolated IOL image 112*i* has a sharp and well-defined contour and IOL edge 8 relative to the dark background. For this reason, in automated video-microscope-based embodiments, there is no need to apply a sophisticated edge recognition software to identify the IOL edge 8 relative to the peripheral illumination light 112*p*'s gray peripheral image. The blocking of the peripheral illumination light 112*p* by the aperture stop 130 automatically performs this separation optically, without a sophisticated software. Of course, the IOL edge 8 still needs to be identified in this isolated IOL image 112*i*, but a simple edge recognition software can perform this job simply, rapidly, and with high accuracy because of the high contrast and high signal-to-noise ratio relative to the dark background.

In non-automated, optical or video-microscope-based embodiments, there is no need for the doctor to strain his eyes to determine where is the IOL edge 8 in a noisy or grainy grey image. Since the isolated IOL image 112*i* has its contour where the IOL 5 has its IOL edge 8, it is qualitatively easier to locate this well-defined and high contrast IOL edge 8 than it was for the combined image 112*c*, and thus subsequently to determine the location of the IOL 5 in the optic reference frame 113 of the optic 120.

FIG. 1A further illustrates that in some embodiments of the ophthalmic visualization system 100, the rear illumination system 110 can include a rear illumination light source 114, positioned off an optical path of the optic 120, to generate the rear illumination light 111, and an illumination light beam splitter 116, to redirect the generated rear illumination light 111 from the rear illumination fight source 114 into the optical path, or visual axis, of the optic 120.

Figure 1B:
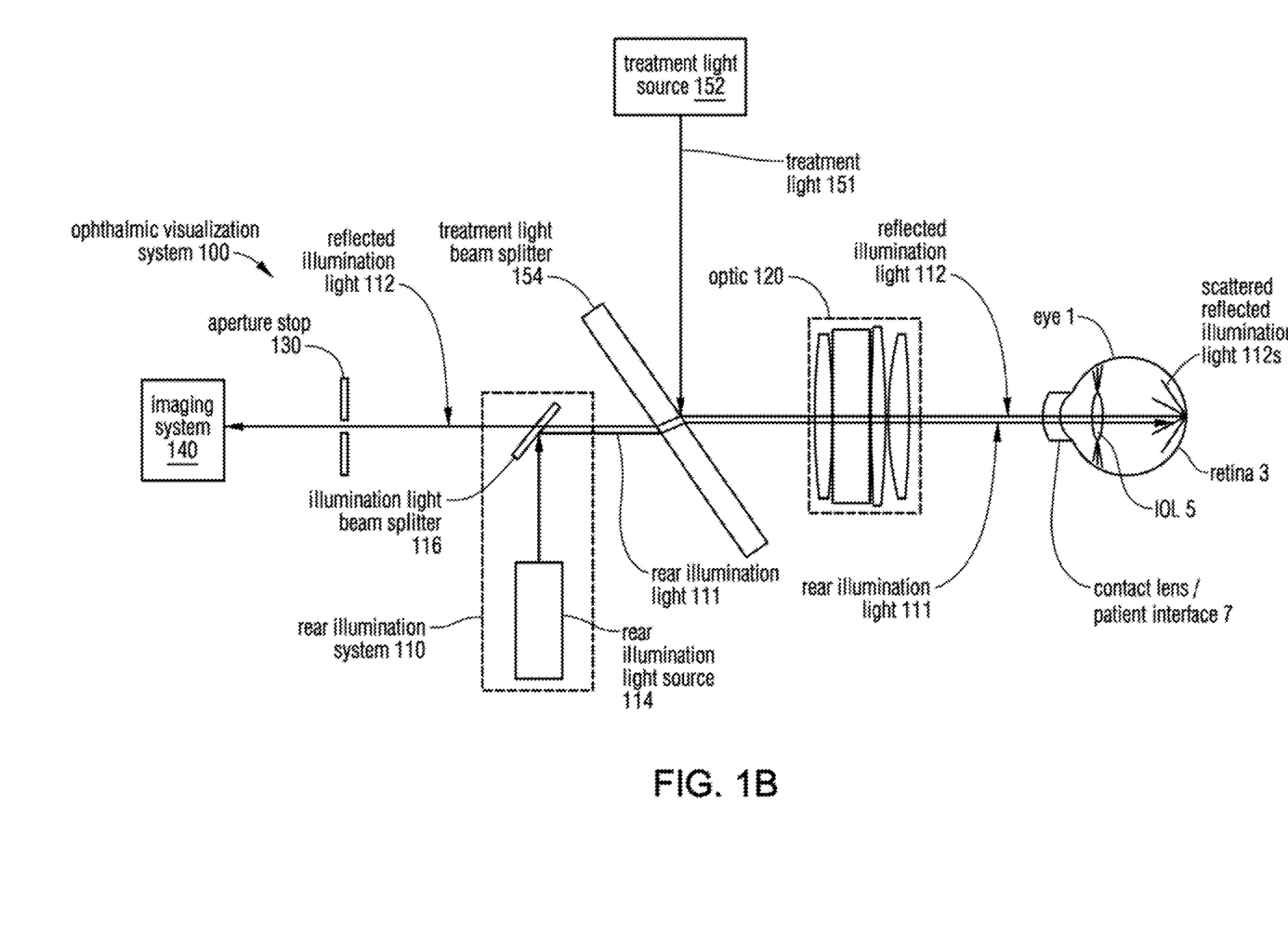

FIG. 1B illustrates a specific embodiment of FIG. 1A, where the optic 120 is shown to include a particular set of lenses.

In embodiments, the rear illumination light source 114 can be configured to generate a red or an infrared rear illumination light 111. A contact lens/patient interface 7 can be placed onto a from cornea of the eye 1 to provide a controlled interface for the rear illumination light 111 to enter the eye 1.

In some embodiments, the aperture slop 130 can be positioned at a location where the peripheral illumination light 112*p*, and the IOL-focused illumination light 112*f* are spatially separated. This location may be in an interval or segment that is only a limited fraction of the overall optical path.

Figure 3C:
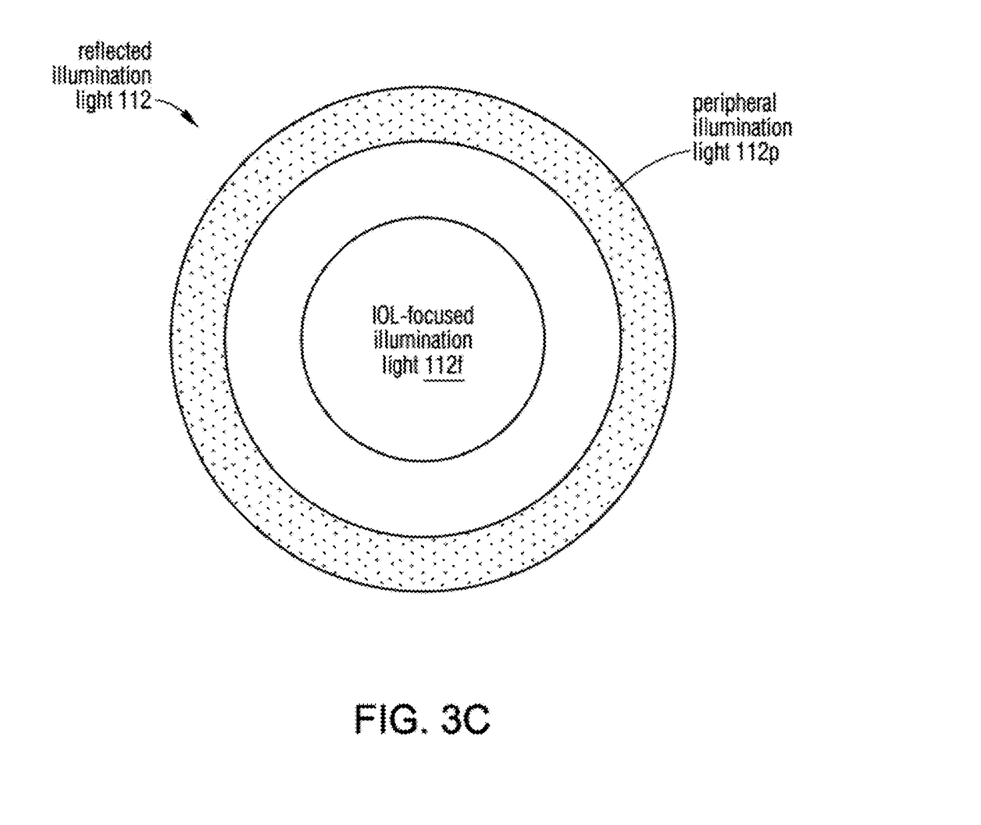

FIG. 3C illustrates a cross-sectional view of the components of the reflected illumination light 112 in the interval of beam separation. In this interval, the peripheral illumination light 112*p* forms an annulus around and distinct from the IOL-focused illumination light 112*f*. This spatial separation of the beam components makes the selective blocking of the peripheral illumination light 112*p* possible, by positioning the aperture stop 130 in this interval.

Figure 4A:
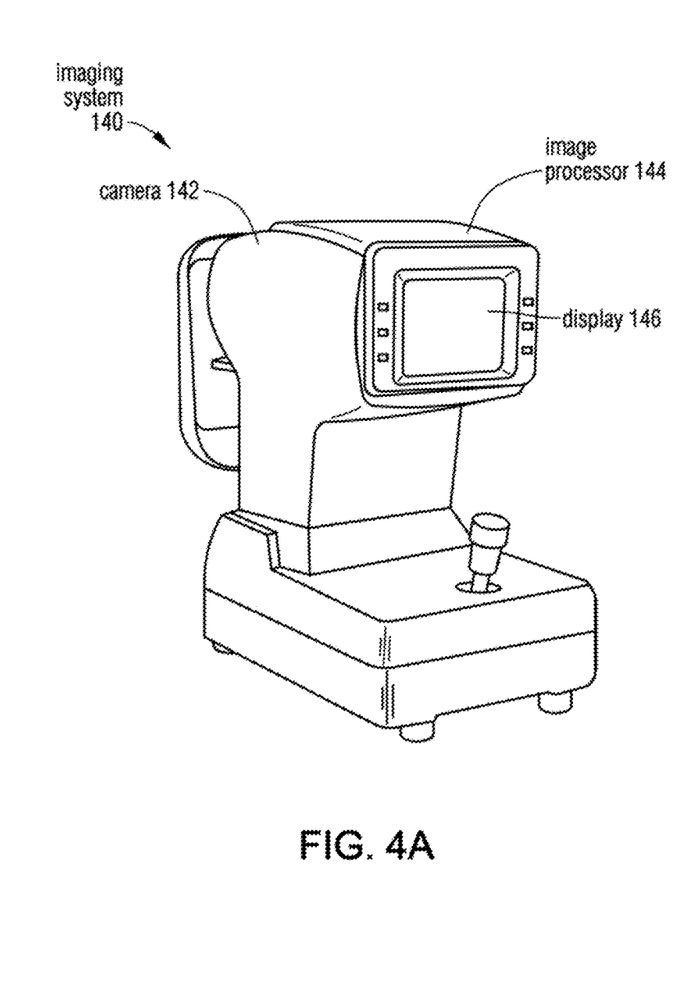
FIGS. 4A-B illustrate embodiments of the imaging system 140.

FIG. 4A illustrates that in embodiments, the imaging system 140 can include a camera 142, to determine a location of the IOL 5 from the isolated IOL image 112*i* in the optic reference frame 113. The camera 142 can include an image processor 144, to determine the location of the IOL 5. As described earlier, this determining of the location of the IOL 5 need not involve an advanced edge recognition software, as the contrast at the IOL edge 8 in FIG. 3B is very pronounced. Once the image processor 144 determines the location of the IOL 5, it can also track a subsequent shift of the location of the IOL 5 in the optic reference frame 113. This feature can be useful if the patient moves his or her eyes during the application of the treatment light 151. Such shifts of the IOL 5 occur in a fraction of the cases and treatments, typically involuntarily, and pose a challenge to keeping the treatment light 151 directed at its intended target. Once a shift of the location of the IOL 5 has been tracked and identified, the doctor can either stop the treatment, or correct the targeting of the treatment light 151, for example by manually moving and realigning the eye 1 with the treatment light 151.

The image processor 144 can track the shift of the location of the IOL 5 by various well-known methods, including by determining a cross correlation using an image of a disk as a kernel. As shown, the image processor 144 can display the determined location of the IOL 5 on a display 146.

Figure 4B:
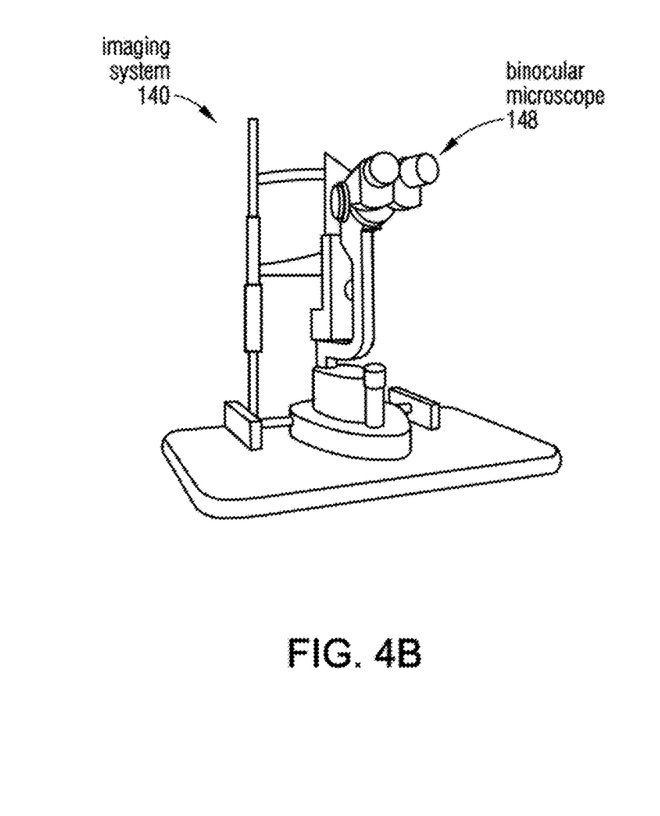

FIG. 4B illustrates another embodiment of the ophthalmic visualization system 100, where the imaging system 140 can include a binocular microscope 148, to form the isolated IOL image 112*i*. In these embodiments, the doctor can view the isolated IOL image 112*i* in at least one of the eye-pieces of the binocular microscope 148, and adjust the treatment light 151, or the patient's eye 1, to properly align, or realign, the treatment light 151 with the eye 1.

Some embodiments can combine the above two: a camera 144 can be implemented in one of the eye pieces of the binocular microscope 148, and a small display 146 can be attached peripherally to the binocular microscope 148, to provide both digitally processed and direct, analog optical imaging for the doctor.

Figure 5:
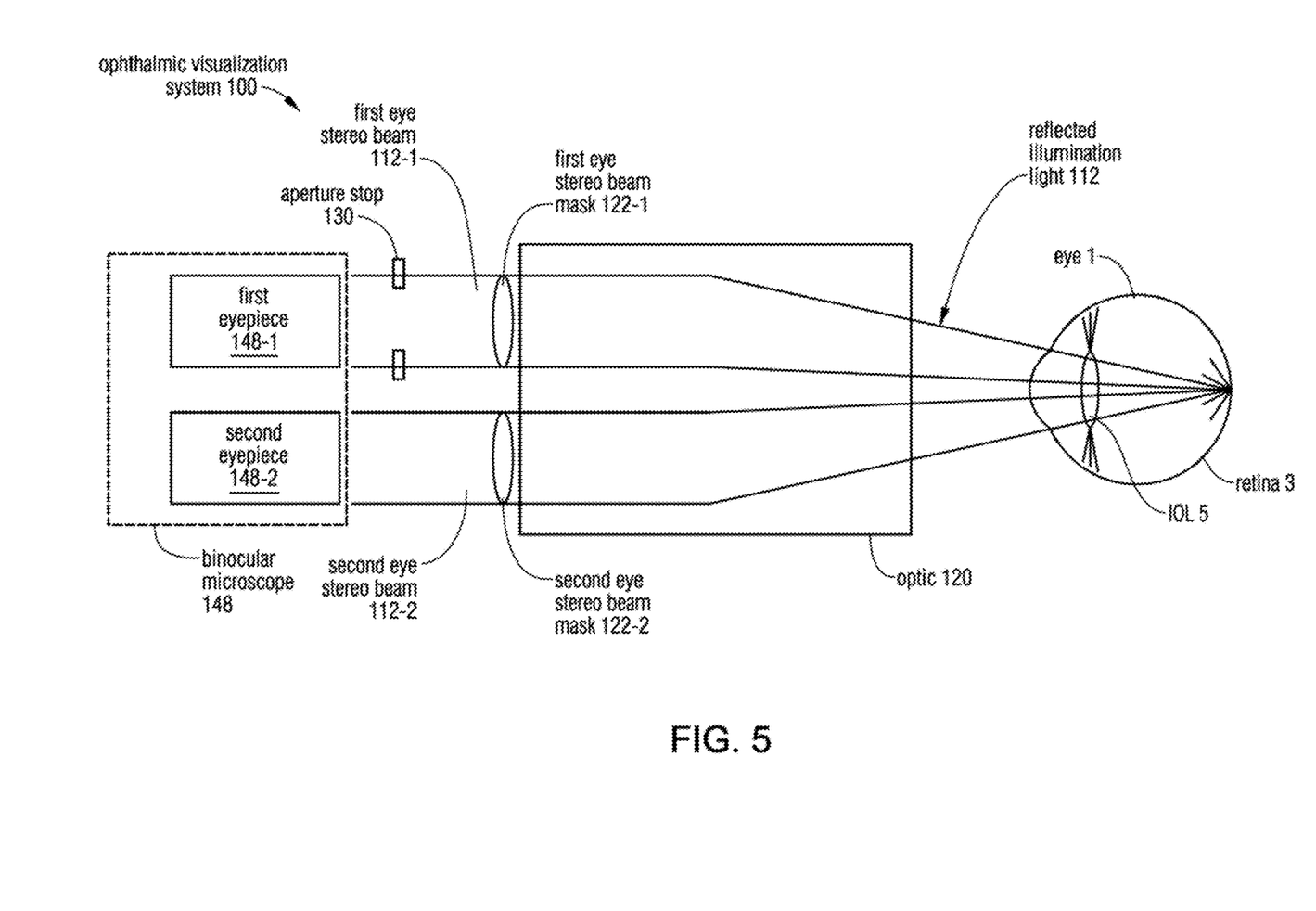
FIG. 5. Illustrates a binocular microscope embodiment of the imaging system 140.

FIG. 5 illustrates a top view of some embodiments of the ophthalmic visualization systems 100 with the binocular microscope 148. This top view is 90 degrees rotated relative to FIG. 1A, which was a side view of the ophthalmic visualization system 100. In this embodiment, the optic 120 can be configured to form, from the reflected illumination light 112, a first eye stereo beam 112-1 for a first eyepiece 148-1 of the binocular microscope 148 with a first eye stereo beam mask 122-1, and a second eye stereo beam 112-2 for a second eyepiece 148-2 of the binocular microscope 148 with a second eye stereo beam mask 122-2.

Figure 6A:
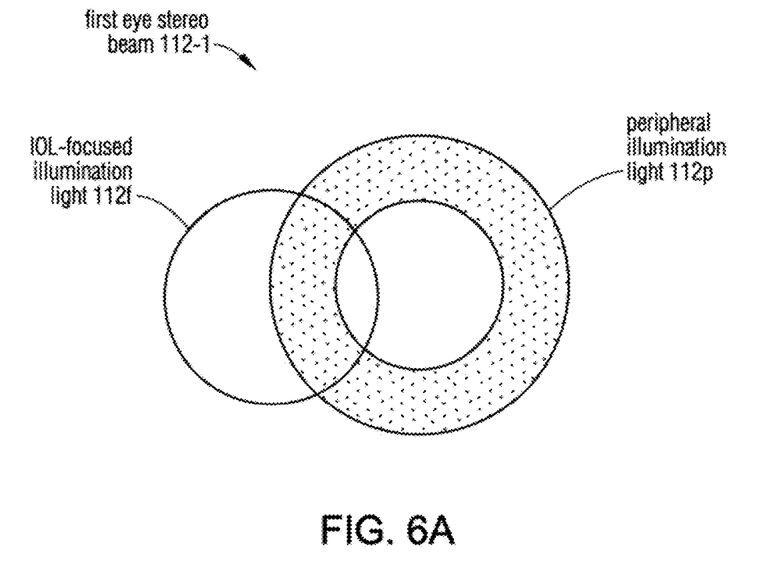
FIGS. 6A-B illustrate shifted IOL images.
Figure 6B:
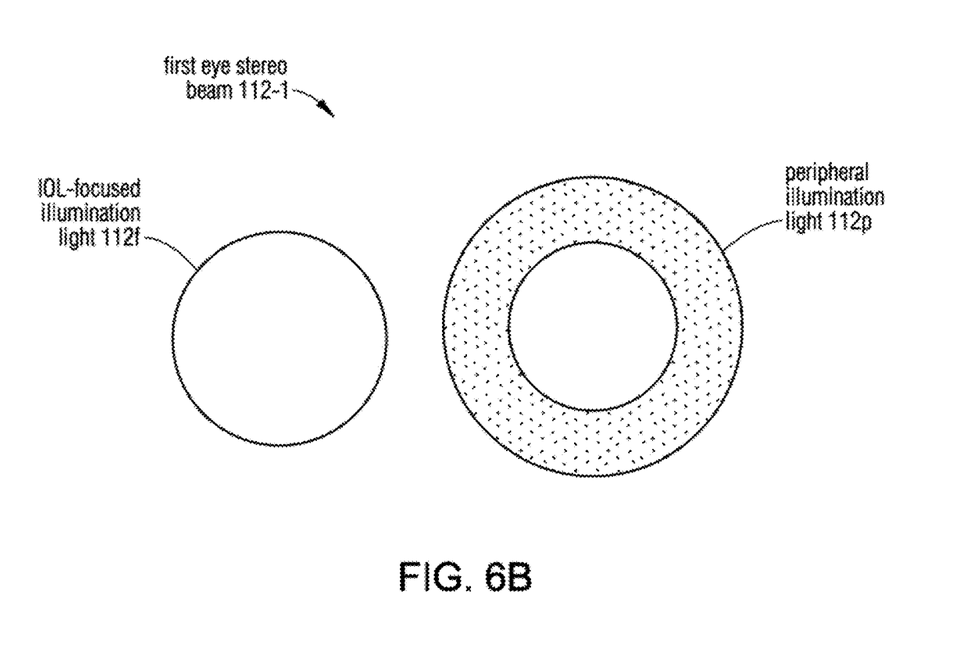

FIGS. 6A-B illustrate that in such embodiments, the aperture stop 130 can be positioned at a location where the peripheral illumination light 112p and the IOL-focused illumination light 112f of one of the first eye stereo beam 112-1 and the second eye stereo beam 112-2 are partially spatially shifted (FIG. 6A), or are fully spatially shifted (FIG. 6B), because the reflected illumination light 112 has been angularly deflected to the off-axis eyepieces 148-1 and 148-2. In the partially shifted embodiments of FIG. 6A, the IOL-focused illumination light 112f may not form a fully isolated IOL image 112i, as an edge or contour of the peripheral illumination light 112p may intersect the isolated IOL image 112i. However, the aperture stop 130 can still be placed at a location such that the IOL-focused illumination light 112f creates an image of the IOL 5 with a sharp IOL edge 8, and therefore, the determination of the IOL position will have the same ease and high accuracy as in other embodiments. In some of these partially shifted embodiments, the aperture stop 130 may block the peripheral illumination light 112p only in a segmented, or partial manner. In the fully shifted embodiments of FIG. 6B, the blocking of the peripheral illumination light 112p with the aperture stop 130 is straightforward.

Returning to FIGS. 1A-B, in some embodiments of the ophthalmic visualization system 100, an object plane of the imaging system 140 can be within a 3 mm vicinity of a plane of the IOL 5, implanted in the eye 1. In some embodiments, the object plane of the imaging system 140 can be within a 1 mm vicinity of a plane of the IOL 5 implanted in the eye 1. In some cases, the optic 120 can be designed so that the object plane of the imaging system 140 can essentially coincide with the plane of the IOL 5.

In some embodiments, as mentioned briefly before, the treatment light system 150 can include the treatment light source 152, positioned off an optical path of the optic 120, to generate the treatment light 151, and a treatment light beam splitter 154, to redirect the generated treatment light 151 from the treatment light source 152 into the optical path of the optic 120. In some embodiments, the treatment light source 152 can be configured to generate an ultraviolet treatment tight for adjusting an optical property of the implanted IOL 5.

Figure 7:
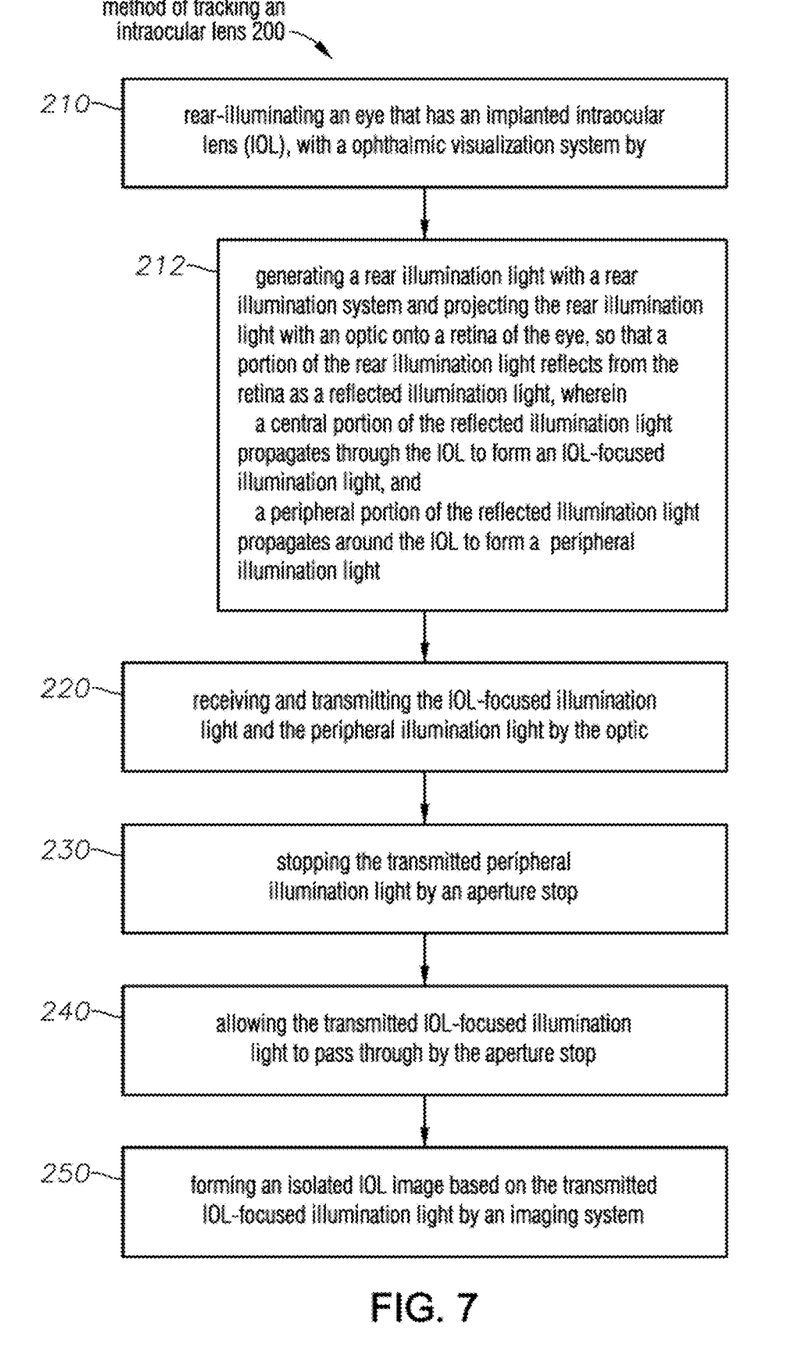
FIG. 7 illustrates a method of tracking an IOL.

FIG. 7 illustrates a method 200 of tracking an intraocular lens IOL 5. The method 200 can include the following steps.

Rear-illuminating 210 an eye 1 that has an implanted intraocular lens, IOL 5, with an ophthalmic visualization system 100, by
generating 212 a rear illumination light 111 with a rear illumination system 110 and projecting the rear illumination light 111 with an optic 120 onto a retina 3 of the eye 1, so that a portion of the rear illumination light 111 reflects from the retina 3 as a reflected illumination light 112, wherein
a central portion of the reflected illumination 112 light propagates through the IOL 5 to form an IOL-focused illumination light 112f, and
a peripheral portion of the reflected illumination light 112 propagates around the IOL to form a peripheral illumination light 112p,
receiving and transmitting 220 the IOL-focused illumination light 112f and the peripheral illumination light 112p by the optic 120;
stopping 230 the transmitted peripheral illumination light 112p by an aperture stop 130;
allowing 240 the transmitted IOL-focused illumination light 112f to pass through by the aperture slop 130; and
forming 250 an isolated IOL image 112i based on the transmitted IOL-focused illumination light 112f by an imaging system 140.

Steps of the method 200 can be practiced according to the embodiments elaborated in relation to FIGS. 1-6 earlier.

Some embodiments of the method 200 can include a determining of a location of the IOL 5 from the isolated IOL image 112i with an image processor 144 of the imaging system 140, in an optic reference frame 113.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and me claimed combination may be directed to another subcombination or a variation of a subcombinations.

The invention claimed is:

1. An ophthalmic visualization system, comprising:
a rear illumination system, to generate and to project a rear illumination light onto a retina of an eye that has an intraocular lens (IOL) implanted into the eye, so that the rear illumination light reflects from the retina as a reflected illumination light, wherein
a central portion of the reflected illumination light propagates through the IOL to form an IOL-focused illumination light, and
a peripheral portion of the reflected illumination light propagates around the IOL to form a peripheral illumination light;
an optic, to receive the IOL-focused illumination light and the peripheral illumination light from the eye, and to transmit the received illumination lights;
an aperture stop, to stop the transmitted peripheral illumination light, and to allow the IOL-focused illumination light to pass through; and
an imaging system, to form an isolated IOL image based on the transmitted IOL-focused illumination light.

2. The ophthalmic visualization system of claim 1, the rear illumination system comprising:
an illumination light source, positioned off an optical path of the optic, to generate the rear illumination light; and
an illumination light beam splitter, to redirect the generated rear illumination light from the illumination light source into the optical path of the optic.

3. The ophthalmic visualization system of claim 1, wherein:
the rear illumination light source is configured to generate one of a red and an infrared rear illumination light.

4. The ophthalmic visualization system of claim 1, wherein:
the aperture stop is positioned at a location where the peripheral illumination light and the IOL-focused illumination light are spatially separated.

5. The ophthalmic visualization system of claim 1, wherein:
the aperture stop is positioned at a location where the peripheral illumination light forms an annulus around and distinct from the IOL-focused illumination light.

6. The ophthalmic visualization system of claim 1, the imaging system comprising:

a camera, to determine a location of the IOL from the isolated IOL image in an optic reference frame.

7. The ophthalmic visualization system of claim 6, the camera comprising:
an image processor, to track a shift of the location of the IOL in the optic reference frame.

8. The ophthalmic visualization system of claim 7, wherein:
the image processor is configured to track the shift of the location of the IOL by determining a cross-correlation using an image of a disk as a kernel.

9. The ophthalmic visualization system of claim 1, the imaging system comprising:
a binocular microscope, to form the isolated IOL image.

10. The ophthalmic visualization system of claim 9, wherein:
the optic is configured to form, from the reflected illumination light,
a first eye stereo beam for a first eyepiece of the binocular microscope, and
a second eye stereo beam for a second eyepiece of the binocular microscope; and
the aperture stop is positioned at a location where the peripheral illumination light and the IOL-focused illumination light of one of the first eye stereo beam and the second eye stereo beam are one of partially spatially shifted, and fully spatially shifted.

11. The ophthalmic visualization system of claim 1, wherein:
an object plane of the imaging system is within a 3 mm vicinity of a plane of the IOL implanted in the eye.

12. The ophthalmic visualization system of claim 1, wherein:
an object plane of the imaging system is within a 1 mm vicinity of a plane of the IOL implanted in the eye.

13. The ophthalmic visualization system of claim 1, comprising:
a treatment light source, positioned off an optical path of the optic, to generate a treatment light; and
a treatment light beam splitter, to redirect the generated treatment light from the treatment light source into the optical path of the optic.

14. The ophthalmic visualization system of claim 13, wherein:
the treatment light source is configured to generate an ultraviolet treatment light for adjusting an optical property of the implanted IOL.

15. A method of tracking an intraocular lens, the method comprising:
rear-illuminating an eye that has an implanted intraocular lens (IOL), with an ophthalmic visualization system by
generating a rear illumination light with a rear illumination system and projecting the rear illumination light with an optic onto a retina of the eye, so that a portion of the rear illumination light reflects from the retina as a reflected illumination light, wherein
a central portion of the reflected illumination light propagates through the IOL to form an IOL-focused illumination light, and
a peripheral portion of the reflected illumination light propagates around the IOL to form a peripheral illumination light;
receiving and transmitting the IOL-focused illumination light and the peripheral illumination light by the optic;
stopping the transmitted peripheral illumination light by an aperture stop;
allowing the transmitted IOL-focused illumination light to pass through by the aperture stop; and
forming an isolated IOL image based on the transmitted IOL-focused illumination light by an imaging system.

16. The method of claim 15, comprising:
determining a location of the IOL from the isolated IOL image with an image processor of the imaging system, in an optic reference frame.

* * * * *